United States Patent [19]
Malcolm et al.

[11] Patent Number: 5,856,501
[45] Date of Patent: Jan. 5, 1999

[54] SYNTHESIS OF THIAZOLE DERIVATIVES

[75] Inventors: Arcelio J. Malcolm; Tse-Chong Wu, both of Baton Rouge, La.

[73] Assignee: Albemarle Corporation, Richmond, Va.

[21] Appl. No.: 989,096

[22] Filed: Dec. 11, 1997

Related U.S. Application Data

[62] Division of Ser. No. 816,111, Mar. 11, 1997, Pat. No. 5,731,442.

[51] Int. Cl.$^6$ ................................................ C07D 277/38
[52] U.S. Cl. ............................................. 548/193
[58] Field of Search ............................................ 548/193

[56] References Cited

U.S. PATENT DOCUMENTS

| | | | |
|---|---|---|---|
| 4,262,126 | 4/1981 | Gilman et al. | 548/193 |
| 4,283,408 | 8/1981 | Hirata et al. | 424/270 |
| 4,347,370 | 8/1982 | Gilman et al. | 548/193 |
| 4,496,737 | 1/1985 | Hoffman, Jr. | 548/193 |
| 4,562,261 | 12/1985 | Hirata et al. | 548/184 |
| 4,609,737 | 9/1986 | Hirata et al. | 548/184 |
| 4,835,281 | 5/1989 | Bod et al. | 548/197 |
| 4,942,243 | 7/1990 | Koh et al. | 548/193 |

FOREIGN PATENT DOCUMENTS

| | | |
|---|---|---|
| 1323032 | of 0000 | Canada . |
| 0284536 | 9/1988 | European Pat. Off. . |
| 0322335 | 6/1989 | European Pat. Off. . |
| 0356366 | 2/1990 | European Pat. Off. . |
| 2007375 | 6/1989 | Spain . |
| 2220415 | 12/1991 | United Kingdom . |

OTHER PUBLICATIONS

Miller et al. "The Preparation of Some Amino Sulfonamides", Journal of the American Chem. Soc., vol 62, Aug. 1940, pp. 2099–2103.

Bauer et al., "Addition of Thiourea to Acrylonitrile and Acrylamides", Journal of Organic Chemistry, May 1961, vol. 26, pp. 1443–1445.

*Primary Examiner*—Johann Richter
*Assistant Examiner*—Laura R.C. Lutz
*Attorney, Agent, or Firm*—Philip M. Pippenger

[57] ABSTRACT

N-[4-(cyanoethylthiomethyl)-2-thiazolyl]guanidine—a key intermediate for preparing the pharmaceutical, famotidine—is produced by mixing in a liquid medium formed from a chemically indifferent organic solvent and water, and under an inert atmosphere, (i) a 2-guanidino-4-halomethylthiazole or a hydrohalide complex thereof, (ii) an S-(2-cyanoethyl) isothiourea or a hydrohalide complex thereof, and (iii) a strong alkali metal base. In lieu of (ii), an alkali metal salt of 2-cyanoethyl-1-thiol can be used, and in such case use of (iii) is optional, but preferable.

10 Claims, No Drawings

SYNTHESIS OF THIAZOLE DERIVATIVES

REFERENCE TO RELATED APPLICATION

This is a division of our prior application Ser. No. 08/816,111, filed Mar. 11, 1997, now U.S. Pat. No. 5,731,442, issued Mar. 24, 1998.

TECHNICAL FIELD

This invention relates to a novel synthesis procedure for the efficient production of a key intermediate useful in the preparation of the pharmaceutical, famotidine.

BACKGROUND

Famotidine is a well-known histamine H2-receptor antagonist and gastric acid secretion inhibitor. A key intermediate for the preparation of this compound is N-[4-(cyanoethylthiomethyl)-2-thiazolyl]guanidine (also known as N-[4-[[(2-cyanoethyl)thio]-methyl]-2-thiazoyl]guanidine).

To prepare this intermediate U.S. Pat. Nos. 4,562,261 and 4,609,737 describe a route based on N-[4-(chloromethyl)-4,5-dihydro-4-hydroxy-2-thiazolyl]guanidine hydrochloride as the starting material. The synthesis involves preparing this starting material by portionwise addition of (aminoiminomethyl)thiourea to dichloroacetone in acetone at temperatures of about −5° to −7° C. and stirring the resultant mixture for 5 days at below 0° C. The resultant N-[4-(chloromethyl)-4,5-dihydro-4-hydroxy-2-thiazolyl] guanidine hydrochloride is isolated, purified and converted to N-[4-[[(2-aminoiminomethyl)thio]-methyl]-2-thiazoyl] guanidine) dihydrochloride by reaction with thiourea. Without isolating this intermediate, the reaction mixture is cooled below 10° C. and to the solution are added β-chloropropionitrile and isopropyl alcohol, followed by dropwise addition of aqueous NaOH whereby crystals of N-[4-(cyanoethylthiomethyl)-2-thiazolyl]guanidine are formed.

SUMMARY OF THE INVENTION

This invention provides novel, highly effective process technology enabling production of N-[4-(cyanoethylthiomethyl)-2-thiazolyl]guanidine of high purity in a clean reaction. Pursuant to one embodiment of this invention N-[4-(cyanoethylthiomethyl)-2-thiazolyl] guanidine is formed by mixing in a liquid medium formed from at least one chemically indifferent organic solvent and water, and under an inert atmosphere, (i) a 2-guanidino-4-halomethylthiazole or a hydrohalide complex thereof, (ii) a S-(2-cyanoethyl)-isothiourea or a hydrohalide complex thereof, and (iii) a strong alkali metal base in proportions and under reaction conditions such that N-[4-(cyanoethylthiomethyl)-2-thiazolyl]guanidine is produced.

Another embodiment of this invention is a process comprising mixing in a liquid medium formed from at least one chemically indifferent organic solvent and water, and under an inert atmosphere:

a) a 2-guanidino-4-halomethylthiazole or a 2-guanidino-4-halomethylthiazole hydrohalide or a combination thereof;

b) an alkali metal salt of 2-cyanoethyl-1-thiol; and c) optionally, but preferably, a strong alkali metal base;

in proportions and under reaction conditions such that N-[4-(cyanoethylthiomethyl)-2-thiazolyl]guanidine is produced.

Other embodiments and features of the invention will be still further apparent from the ensuing description and appended claims.

FURTHER DETAILED DESCRIPTION

The Product

N-[4-(cyanoethylthiomethyl)-2-thiazolyl]guanidine can be represented by the formula:

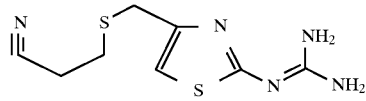

It will be appreciated that the guanidine moiety is capable of undergoing tautomerization to a terminal —NH—C(—NH$_2$)(=NH) moiety.

2-Guanidino-4-Halomethylthiazole Reactant

This reactant is a 2-guanidino-4-halomethylthiazole or a 2-guanidino-4-halomethylthiazole hydrohalide or a combination thereof. The halogen atoms in these compounds are preferably chlorine or bromine atoms as these compounds exhibit suitably high reactivity in the process and they are the most cost-effective of the group. The iodide derivatives, while usable, are more expensive. Thus the preferred thiazole reactants are 2-guanidino-4-chloromethylthiazole, 2-guanidino-4-chloromethylthiazole hydrochloride, 2-guanidino-4-bromomethylthiazole, and 2-guanidino-4-bromomethylthiazole hydrobromide. Mixtures of two or more of these can be used, if desired. These compounds are illustrated by the following formula of 2-guanidino-4-bromomethylthiazole hydrobromide:

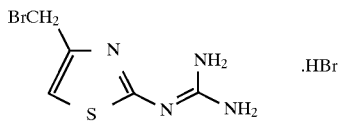

It is again to be noted that the guanidine moiety is capable of undergoing tautomerization to a terminal —NH—C(—NH$_2$)(=NH) moiety.

The 2-guanidino-4-halomethylthiazole reactants can be prepared by reaction between a 1,3-dihaloacetone such as 1,3-dichloroacetone or 1,3-dibromoacetone with 2-imino-4-thiobiuret in a polar solvent such as a liquid ketone, preferably acetone. This reaction tends to be an exothermic reaction. Thus to assist is temperature control, it is desirable to pre-cool at least the polar solvent (which may contain either reactant, preferably the 1,3-dihaloacetone) to a temperature in the range of about 0° to about 10° C. before initiating the feed of the two reactants, or the feed of the second reactant to be fed. Upon initiation of the reaction, the exotherm will heat up the reaction mixture to desirable or at least readily controllable temperatures. The reaction mixture should be agitated as by use of a mechanical stirrer to ensure thorough mixing of the reactants within the reaction mixture. Reaction periods are typically in the range of about 1 to about 24 hours, and preferably in the range of about 1 to about 8 hours.

S-(2-Cyanoethyl)isothiourea Reactant

In one embodiment of this invention, the other reactant is S-(2-cyanoethyl)isothiourea or a hydrohalide complex thereof, again with the hydrochloride or hydrobromide complexes being preferred. Details concerning the synthesis of such compounds are given in L. Bauer and T. L. Welsh, *J. Org. Chem.*, 1961, 26, 1443–1445. See also E. Miller, J. M.

Sprague, L. W. Kissinger and L. F. McBurney, *J. Am. Chem. Soc.,* 1940, 62, 2100–3103.

Alkali Metal 2-Cyanoethyl-1-Thiolate Reactant

In another embodiment of this invention an alkali metal salt of 2-cyanoethyl-1-thiol, which can also be named as an alkali metal 2-cyano-1-thiolate. Such compounds can be depicted by the formula:

where M is the alkali metal cation. These compounds can be formed by reaction of equimolar amounts of S-(2-cyanoethyl)isothiourea and a strong base such as NaOH or KOH, or by reaction of two moles of such strong base per mole of S-(2-cyanoethyl)isothiourea hydrohalide. Another method is to react an alkali metal with 2-cyanoethyl-1-thiol.

Strong Base

In most of the above embodiments the reaction is performed in the presence of a strong alkali metal base. Suitable compounds that can be used include sodium oxide, sodium hydroxide, potassium oxide and potassium hydroxide. Mixtures of two or more of these can be used, if desired. As is well known, the addition of an alkali metal oxide to an aqueous medium will result in formation of an alkali metal hydroxide solution. In addition, in an aqueous medium the alkali metal hydroxides are ionized such that alkali metal cations and hydroxyl anions are present in the medium. When an alcohol is co-present, the possibility may exist for equilibria to arise involving alkali metal alkoxide formation as well. While chemists are aware of these things, it is deemed prudent, if not necessary, to mention this for the benefit of those who may not have skill in the chemical arts.

The amount of base used depends to some extent upon the reactants with which it is used. Thus if the reactants used are an equimolar mixture of 2-guanidino-4-halomethylthiazole hydrohalide and an S-(2-cyanoethyl)isothiourea hydrohalide, at least 3 moles of alkali metal hydroxide (or oxide) per mole of each reactant should be used, 2 moles being used to neutralize the hydrogen halide of each reactant, and the remaining mole being used to convert the S-(2-cyanoethyl)isothiourea to alkali metal 2-cyano-1-thiolate. If one of these two reactants is present in free form (i.e., it has no hydrogen halide complexed therewith), at least 2 moles of alkali metal hydroxide (or oxide) per mole of each reactant should be used, 1 mole being used to neutralize the hydrogen halide of the reactant used as the hydrohalide complex, and the remaining mole being used to convert the S-(2-cyanoethyl)isothiourea to alkali metal 2-cyano-1-thiolate. If both of these reactants are used in free form, then at least one mole of alkali metal hydroxide (or oxide) per mole of the S-(2-cyanoethyl)isothiourea should be used in order to convert the S-(2-cyanoethyl)isothiourea to alkali metal 2-cyano-1-thiolate. Preferably a small excess amount of the alkali metal base over the stoichiometric amounts (e.g., 10 mole % excess) is desirable.

If the reactants used are an equimolar mixture of 2-guanidino-4-halomethylthiazole hydrohalide and an alkali metal salt of 2-cyanoethyl-1-thiol, at least one mole of alkali metal base should be used in order to neutralize the hydrogen halide present. When the reactants are an equimolar mixture of 2-guanidino-4-halomethylthiazole and an alkali metal salt of 2-cyanoethyl-1-thiol, use of a strong base is not essential, but the use of a small amount (e.g., 0.1 mole per mole of the 2-guanidino-4-halomethylthiazole) is recommended.

Reaction Media

To form this product the reaction between the above reactants is performed in a medium composed of a mixture of water and a suitable chemically indifferent organic solvent, which thus does not materially interfere with the desired reaction.

Organic solvents that can be used in forming the reaction medium include alkanols having 3 or more carbon atoms in the molecule (e.g., 1-propanol, 2-propanol, 1-butanol, 1-methyl-1-propanol, 2-methyl-1-propanol, and the like), ethers (e.g., 1,2-dimethoxyethane, propyl ether, isopropyl ether, tetrahydrofuran, 2-methyltetrahydrofuran, 1,3-dioxolane, and the like), and ketones (e.g., acetone, methyl ethyl ketone, 2-pentanone, 3-pentanone, and the like. Mixtures of one or more such solvents can be used. Of the alkanols, secondary alkanols are preferred. The reaction can be performed in a two-phase liquid medium by suitably agitating the reaction mixture to ensure intimate contact between the reactants. However, use of a one-phase liquid medium is preferred. Accordingly, preferred organic solvents are those that form a homogeneous one-phase liquid medium at 25° C. when mixed with the amount of water being used in forming the reaction medium. In addition, the preferred solvents are those that at ordinary atmospheric pressure are liquids over the range of −15° C. to 150° C. and that boil at one or more temperatures below about 150° C. at 760 mm Hg pressure, as such relatively high volatility can be utilized to facilitate their removal after they have served their purpose as a suitable liquid medium in which to conduct the reaction. Most preferred as the solvent is 2-propanol because of its highly suitable physical properties, inertness in the reaction, low cost and ready availability.

Proportions of the organic solvent and water typically fall in the range of about 0.1 to about 10 parts by weight of organic solvent per part by weight of water.

Other Reaction Conditions

In order to minimize formation of impurities, it is desirable to carry out all operations under an inert atmosphere such as under nitrogen or other inert gas. In addition it is desirable to remove air that may be entrained in the organic solvent and/or in the water used in forming the reaction medium.

The reaction for the preparation of N-[4-(cyanoethylthiomethyl)-2-thiazolyl]guanidine pursuant to this invention is usually initiated at a temperature in the range of about −15° to about 50° C. and preferably in the range of about 0° to about 25° C. Thus it is desirable to pre-cool at least the solvent (which may contain either one of the reactants, and/or the strong alkali metal base) to a temperature in one of the foregoing ranges before initiating the feed of the other component(s). The reaction mixture should be agitated as by use of a mechanical stirrer to ensure thorough mixing of the reactants within the reaction mixture.

While the two reactants and the base can be fed concurrently and/or sequentially and individually or in various subcombinations, it is preferred when conducting the embodiment wherein S-(2-cyanoethyl)isothiourea or a hydrohalide thereof is used as the reactant, to form a solution of this reactant in the solvent-water medium selected for use, mix the strong alkali metal base with this solution, and then add to the resultant mixture the 2-guanidino4-halomethylthiazole reactant (most preferably as a solution in another portion of the same solvent-water medium selected for use). Such addition should be a controlled portionwise addition, with the feed being slow but continuous and/or intermittent. The reaction mixture should be well agitated during this operation.

The period during which the mixture is kept in the range of about −15° to about 25° C. with agitation typically falls in the range of about 1 to about 60 minutes. Then the temperature is allowed or caused to reach ambient room temperature or higher (e.g., at one or more temperatures in the range of about 25° to about 50° C.) and is agitated under these temperature conditions for a period in the range of 0.1 to about 24 hours.

Product can be crystallized from the reaction mixture by seeding at −15° to 35° C. Another method of isolation of product involves distilling the solvent from the product.

Removal of the organic solvent, co-products if any, and water is best effected by conducting a vacuum distillation, which, depending on the solvent(s) employed, typically involves temperatures in the range of about 0° to about 100° C. and pressures in the range of about 5 to about 760 mm-Hg. The solvent removed from the reaction mixture in this operation can be recycled for re-use in the process. The desired product can be washed with water to remove residual inorganic salts.

The following example, wherein all percentages are by weight, illustrate the practice and advantages of this invention, and are not to be construed as constituting limitations on the invention.

EXAMPLE

4-Chloromethyl-2-guanidinothiazole hydrochloride (CGT) (454 mg, 2.00 mmole) was charged to a 10-mL flask in a dry box. A mixture of 2-propanol and water (1:1 w/w, degassed, 3 mL) was added to dissolve the CGT. S-(2-cyanoethyl)isothiourea hydrochloride (CIT) (331 mg, 2.00 mmol) was charged to a 25-mL flask in a dry box. A mixture of 2-propanol and water (1:1 w/w, degassed, 9 mL) was added to dissolve the CIT. The mixture was cooled to 0° C. and sodium hydroxide (25 wt %, 0.98 g, 6.10 mmol) was added over a 5-minute period. After the addition of sodium hydroxide, the mixture was stirred at 0° C. for 30 minutes. The CGT solution was added via a syringe to the CIT solution over a 5-minute period. The mixture was slowly warmed to room temperature and was stirred overnight. LCMS and NMR showed the clean nitrile product.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

What is claimed is:

1. A process comprising mixing in a liquid medium formed from at least one chemically indifferent organic solvent and water, and under an inert atmosphere:
    a) a 2-guanidino-4-halomethylthiazole or a 2-guanidino-4-halomethylthiazole hydrohalide or a combination thereof;
    b) an alkali metal salt of 2-cyanoethyl-1-thiol; and
    c) at least when a) is a 2-guanidino-4-halomethylthiazole hydrohalide or is said combination which includes a 2-guanidino-4-halomethylthiazole hydrohalide, a strong alkali metal base;
in proportions and under reaction conditions such that N-[4-(cyanoethylthiomethyl)-2-thiazolyl]guanidine is produced.

2. A process according to claim 1 wherein said base consists essentially of sodium oxide or hydroxide, or potassium oxide or hydroxide, and wherein said solvent consists essentially of a liquid secondary alkanol.

3. A process according to claim 1 wherein a) is 2-guanidino-4-chloromethylthiazole hydrochloride or 2-guanidino-4-bromomethylthiazole hydrobromide or a combination thereof, and wherein b) is a sodium or potassium salt of 2-cyanoethyl-1-thiol.

4. A process according to claim 3 wherein said base consists essentially of sodium oxide or hydroxide, or potassium oxide or hydroxide, and wherein said solvent consists essentially of 2-propanol.

5. A process which comprises forming in a liquid medium formed from at least one chemically indifferent organic solvent and water, and under an inert atmosphere, a mixture of:
    a) a 2-guanidino-4-halomethylthiazole or a 2-guanidino-4-halomethylthiazole hydrohalide or a combination thereof;
    b) an alkali metal salt of 2-cyanoethyl-1-thiol; and
    c) at least when a) is a 2-guanidino-4-halomethylthiazole hydrohalide or is said combination which includes a 2-guanidino-4-halomethylthiazole hydrohalide, a strong alkali metal base;
in proportions and under reaction conditions such that N-[4-(cyanoethylthiomethyl)-2-thiazolyl]guanidine is produced.

6. A process according to claim 5 wherein said base consists essentially of sodium oxide or hydroxide, or potassium oxide or hydroxide, and wherein said solvent consists essentially of a liquid secondary alkanol.

7. A process according to claim 5 wherein a) is 2-guanidino-4-chloromethylthiazole hydrochloride or 2-guanidino-4-bromomethylthiazole hydrobromide or a combination thereof, and wherein b) is a sodium or potassium salt of 2-cyanoethyl-1-thiol.

8. A process according to claim 7 wherein said base consists essentially of sodium oxide or hydroxide, or potassium oxide or hydroxide, and wherein said solvent consists essentially of 2-propanol.

9. A process according to claim 6 wherein said base consists essentially of sodium oxide or hydroxide, and wherein said solvent consists essentially of 2-propanol.

10. A process according to claim 7 wherein said base consists essentially of sodium oxide or hydroxide, or potassium oxide or hydroxide, and said solvent consists essentially of a liquid secondary alkanol.

* * * * *